United States Patent [19]

Mihailovski

[11] 4,084,062
[45] * Apr. 11, 1978

[54] ACETYLENIC 2,6-DICHLOROBENZOATES AS PLANT GROWTH REGULATORS

[75] Inventor: Alexander Mihailovski, Kensington, Calif.

[73] Assignee: Stauffer Chemical Company, Westport, Conn.

[*] Notice: The portion of the term of this patent subsequent to Dec. 7, 1993, has been disclaimed.

[21] Appl. No.: 750,313

[22] Filed: Dec. 14, 1976

Related U.S. Application Data

[63] Continuation of Ser. No. 504,574, Sep. 9, 1974, abandoned.

[51] Int. Cl.² ............................................. C07C 69/78
[52] U.S. Cl. .................................. 560/106; 560/112; 560/113; 71/107
[58] Field of Search ............... 260/476 R; 560/106, 560/113

[56] References Cited

U.S. PATENT DOCUMENTS

| | | | |
|---|---|---|---|
| 2,340,701 | 2/1944 | Schlichting et al. | 260/476 |
| 2,648,702 | 8/1953 | De Garmo et al. | 260/476 |
| 3,996,379 | 12/1976 | Michailovski | 260/476 |

OTHER PUBLICATIONS

Buta, et al., as cited in Chem. Abstracts, 73, 24122z (1970).

*Primary Examiner*—Jane S. Myers
*Attorney, Agent, or Firm*—Michael J. Bradley

[57] ABSTRACT

This invention relates to the utility of compounds having the general formula

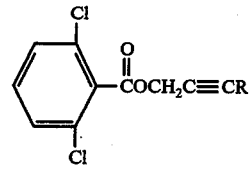

wherein R is selected from the group consisting of —H, —CH₃,

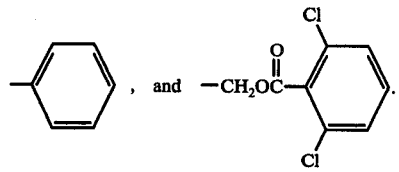

Said compounds are useful as plant growth regulators.

3 Claims, No Drawings

ACETYLENIC 2,6-DICHLOROBENZOATES AS PLANT GROWTH REGULATORS

This is a continuation, of application Ser. No. 504,574 filed Sept. 9, 1974, now abandoned.

BACKGROUND OF THE INVENTION

This invention relates to the use of compounds having the general formula

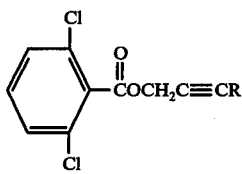

wherein R is selected from the group consisting of —H, —CH₃,

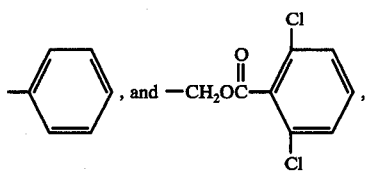

as plant growth regulators.

In general, plant growth regulation is accomplished by either growth stimulation at one or more of the customary growth sites, by roots, buds of flowers or by causing plant deformations such as stunting, defoliation or other malformations designed to change the plant growth characteristics to achieve greater yield of product.

It is desirable to effect growth regulating characteristics in various plants. A wide variety of plant growth regulating properties of certain growth regulating compounds can be observed depending upon the concentration used, the formulation used, and the type of plant species treated with compounds having such growth regulating properties. For example, these compounds are capable of increasing of beneficial or desirable features of crops such as induction of sprouting underground rhizomes of monocotyledonous plants and the induction of rooting when applied to cut ends of plants. Other plant growth regulation activities which are desirable include control of apical dominance; increase in branching on a variety of plant species; increase in protein content of plants by measurable increase of the leaf area relative to the stem area; retardation of terminal growth; increased flowering and fruiting of ecomonic crops; prevention of lodging whereby thicker stems are produced, thus resulting in firmer and stronger plants capable of resisting natural tendencies towards lodging; stimulation of seed germination; and causing hormone or epinasty effects on plants so treated.

The compounds of the present invention may be utilized on a wide variety of plant species at various concentrations of active ingredients. Amounts of as little as 0.1 lb/acre of compound may be used. Moreover, the normal range of concentrations can be from 0.1 lb/ to 16 lbs/acre. The precise amount of acetylenic 2,6-dichlorobenzoates of this invention which should be employed in order to realize the greatest effects will depend upon the particular plant species being treated. In this regard, amounts from about 0.1 lb. to as much as 25–30 lbs/acre, when applied to the plants, will result in the desired plant response, depending upon the total amount of compound used as well as the particular plant species which is being treated. It can be considered, therefore, that the preferred range within the present invention is rates of ½ to 4 lbs/acre in solution such that the application rate in terms of total volume varies from about 10 to 100 gallons per acre.

Although the preferred method of application of the compounds of this invention is directed to the foliage and stems of plants, it has been found that such compounds may be applied to the soil in which the plants are growing. In such cases, the compounds will be root absorbed to a sufficient extent so as to result in plant responses in accordance with the teachings of this invention. In general, the compounds of the present invention can be produced by a process as follows:

General Procedure

In general, the 2,6-dichlorobenzoate esters described herein can be prepared by standard procedures from 2,6-dichlorobenzoyl chloride and an acetylenic alcohol using a base acceptor chosen from the tertiary amines, metal hydrides, or alkali or alkaline earth hydroxides. Reactions can be conducted at temperatures from −10° to 200° C. The liquid tertiary amines can also serve as solvents when used in excess.

The following examples are illustrative of a method for preparing specific compounds of this invention which are used in the plant growth regulating process of this invention.

EXAMPLE I

2-Butyn-1-yl 2′,6′-dichlorobenzoate

To a solution of 3.8 g. (0.052 mole) 2-butyn-1-ol in 30 ml. pyridine held at 0° C was added a benzene solution of 2,6-dichlorobenzoyl chloride made by refluxing 10 g. (0.052 mole) 2,6-dichlorobenzoic acid and 6.8g. (0.057 mole) thionyl chloride. The reaction mixture was held at 0° C for an additional 17 hours and then poured over crushed ice. The resulting solid 2-butyn-1-yl 2′,6′-dichlorobenzoate was filtered, washed and dried. Yield 10 g. (79% based on theory). Structure was confirmed by NMR.

EXAMPLE II

2′,6′-Dichlorobenzoyl 1,4-dioxy-2-butyne

The listed compound was prepared by the procedure of Example I in quantitive yield from a benzene solution of 4.0 g. 2,6-dichlorobenzoyl chloride and a pyridine solution of 0.8 g. 2-butyn-1,4-diol. Structure was confirmed by NMR.

The specific and novel compounds useful in the plant growth regulating process of this invention are shown in Table I below.

TABLE I

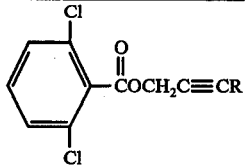

| Compound No. | R. |
| --- | --- |
| 1 | —CH₃ |

TABLE I-continued

[Structure: 2,6-dichlorophenyl group with -COCH$_2$C≡CR substituent]

| Compound No. | R |
|---|---|
| 2 | -H |
| 3 | [phenyl group] |
| 4 | -CH$_2$OC(=O)-(2,6-dichlorophenyl) |

The following examples, compounds of this invention will be referred to by compound number as shown in Table I.

EXAMPLE III

Primary Growth Regulator Evaluation

Compounds included in this evaluation were those that received a BGR (bean growth regulator) designation in the 8 lb/A post-emergence herbicide screen. The compounds were evaluated as a 3 lb/A post-emergence spray at 120 gal/A on two week old seedlings. Test species were cucumbers, pinto beans and soybeans which, at time of spraying, were in th first true leaf, first trifoliate leaf and cotyledon stage of development respectively. The tests were conducted in 6 inch × 9.5 inch × 3 inch plastic flats filled with a loamy sand soil. The seeds were planted ¼ inch deep in rows across the width of the flat (one row per species with 4 to 5 seeds per row). The plants were thinned to two per row prior to spraying. For the application 300 mg. ai of compounds were dissolved in 50 ml. acetone containing 1% Tween 20 ® (other solvents not to exceed 5 ml. were used as needed to dissolve the compounds) and then diluted to 100 ml. with water. Spraying was conducted with a spray table containing one Teejet 8004E nozzle traveling at 0.67 mph.

Treatments were rated three weeks after spraying. Parameters used in rating were as follows:
Tip kill of apical meristem — TK
Shortening of internodes — SI
Plant stunting — ST
Leaf burn — LB
Plant malformation — MF
A) Ratings were - = no effect, + = 10–30%, ++ = 40–60%, +++ = 70–80%, ++++ = 90–100%.

The above parameters are indicators of how a compound might alter the growth characteristic of a plant so as to improve its production capabilities, harvestability or reduce its maintenance requirements.

TABLE II

| Compound Number | II-A PINTO BEANS | | | | |
|---|---|---|---|---|---|
| | MF | ST | LB | SI | TK |
| 1 | +++ | ++++ | − | ++++ | +++ |
| 3 | − | − | − | − | − |
| 4 | ++++ | ++++ | − | ++++ | ++++ |

| Compound Number | SOY BEANS II-B | | | | |
|---|---|---|---|---|---|
| | MF | ST | LB | SI | TK |
| 1 | ++++ | ++++ | − | ++++ | ++++ |
| 3 | + | + | − | − | − |
| 4 | ++++ | ++++ | +++ | ++++ | +++ |

| Compound Number | CUCUMBERS II-C | | | | |
|---|---|---|---|---|---|
| | MF | ST | LB | SI | TK |
| 1 | ++++ | ++++ | − | ++++ | +++ |
| 3 | − | + | − | + | − |
| 4 | ++++ | ++++ | − | ++++ | +++ |

EXAMPLE IV

Evaluation of Potential Growth Regulators on Soybeans

Compounds which have shown some growth regulating properties or are analogs of potential growth regulators were selected for evaluation as a 0.5 and 1.0 lb/A ai post-emergence spray (80 gal/A) to five week old soybean plants (3 to 4 leaf stage of development). Treatments were evaluated for percent malformation and percent stunting six weeks after application.

Dixie T5-09 plastic tubs with perforated bottoms were filled with a loamy sand soil pretreated with 50 ppm. Captam 50W ® and 18. 18. 18 soluable fertilizer. Five soybean seeds were planted 0.5 inches deep into the soil. The containers were placed in a greenhouse and the soil irrigated sufficiently to insure good germination and growth of the soybeans. Five weeks after planting the soybeans were thinned to one plant per tub. Compounds were applied on a liner spray table. Desired application rates of 0.5 and 1.0 lb/A ai were obtained by weighing 75 to 150 mg. ai of compound into 120 ml. bottles, dissolving with 50 ml. of acetone containing 1% Tween 20 ®, and diluting to 100 ml. with water. After spraying the tubs were returned to a greenhouse and irrigated as needed without wetting the foliage for three days. Thereafter, standard irrigation procedures were followed. Six weeks after treatment the plants were rated visually for percent malformation and stunting in relation to Triiodobenzoic acid.

It should be noted that the 0.5 and 1.0 lb. evaluation were done on five week old plants, where as the 3 lb. tests described previously were conducted with plants that were only two weeks old. The age of the plants has a direct bearing on symptom manifestation and in many cases younger plants will not show the effect of growth regulators as noticeably as older plants. Results are shown in Table III below. Triiodobenzoic acid, a known plant growth regulator was evaluated for comparison purposes only.

TABLE III

| Compound Number | ½ lb/A | | 1 lb./A | |
|---|---|---|---|---|
| | %MF | %ST | %MF | %ST |
| 1 | 30 | 55 | 80 | 80 |
| 2 | 40 | 70 | 99 | 100 |
| 3 | 85 | 100 | 98 | 100 |
| 4 | 80 | 90 | 90 | 100 |
| Triiodobenzoic Acid | 10 | 80 | 10 | 90 |

EXAMPLE V

Evaluation of Potential Growth Regulators on Soybeans

Compounds from Example IV above were re-evaluated at the lower application rates of ⅛, ¼ and ½ lb/A ai postemergence spray (80 gal/A) to five week old soybean plants (3 to 4 leaf stage of development). Treatments were evaluated for percent malformation, percent stunting and for number of pods per plant six weeks after application.

Dixie T5-09 plastic tubs with perforated bottoms were filled with a loamy sand soil pretreated with 50 ppm. Captam 50W ® and 18. 18. 18 soluable fertilizer. Five soybean seeds were planted 0.5 inches deep into the soil. The containers were placed in a greenhouse and the soil irrigated sufficiently to insure good germination and growth of the soybeans. Five weeks after planting the soybeans were thinned to one plant per tub. Compounds were applied on a liner spray table. Desired application rates of ⅛, ¼ and ½ lb/A ai were obtained by weighing 18.75 to 75 mg ai of compound into 120 ml. bottles, dissolving with 50 ml. of acetone containing 1% Tween 20 ®, and diluting to 100 ml. with water. After spraying the tubs were returned to a greenhouse and irrigated as needed without wetting the foliage for three days. Thereafter, standard irrigation procedures were followed. Six weeks after treatment the plants were rated visually for percent malformation and stunting in relation to an untreated check. The number of soybean pods were also counted and recorded.

It should be noted that the 0.5 and 1.0 lb. evaluations were done on five week old plants, whereas the 3 lb. tests described previously were conducted with plants that were only two weeks old. The age of the plants has a direct bearing on symptom manifestation and in many cases younger plants will not show the effect of growth regulators as noticeably as older plants. Results are shown in Table IV below.

TABLE IV

| Compound Number | 1/8 lb/A | | |
|---|---|---|---|
| | %MF | %ST | Yield Pod/Plant |
| 1 | | | |
| 2 | 20 | 20 | 10 |
| 3 | 10 | 0 | 17 |
| 4 | 20 | 0 | 16 |
| | 1/4 lb/A | | |
| | %MF | %ST | Yield Pod/Plant |
| 1 | 20 | 30 | 10 |
| 2 | 70 | 50 | 13 |
| 3 | 30 | 50 | 12 |
| 4 | 30 | 60 | 20 |
| | 1/2 lb/A | | |
| | %MF | %ST | Yield Pod/Plant |
| 1 | 50 | 60 | 8 |
| 2 | 70 | 60 | 7 |
| 3 | 80 | 70 | 24 |
| 4 | 60 | 80 | 30 |
| 4 | 60 | 80 | 30 |
| Untreated Control | 0 | 0 | 11–19 |

Application of the acetylenic 2,6-dichlorobenzoates of this invention may be made employing the procedures normally used for treatment of plants including dip or soak treatment of tubers, bulbs or cuttings, for example, as well as foliar, bark or stem or soil application. The active ingredient may be utilized in diverse formulations, including the adjuvants and carriers normally employed for facilitating the dispersion of active ingredients for agricultural applications, recognizing the known fact that the formulation and mode of application of a chemical agent may affect its activity in any given application. Thus, acetylenic 2,6-dichlorobenzoates may be formulated as a solution or dispersion in a non-aqueous medium, as a powdery dust, as a wettable powder, as an emulsifiable concentrate, as a granule or as any of several other known types of formulations, depending upon the desired mode of application. These growth regulatory compositions may be applied as dusts, sprays, dips or granules in the sites in which growth regulation is desired. These formulations may contain as little as 0.0005% or as much as 95% or more by weight of active ingredient and applications may be at rates equivalent to less than one-half to over 80 pounds per acre.

Dusts are admixtures of the active ingredient with finely-divided solids such as talc, attapulgite clay, kieselguhr and other organic and inorganic solids which act as dispersants and carriers for the regulant. These finely divided solids have an average particle size of less than 50 microns. A typical dust formulation useful herein is one containing 1.0 part of an acetylenic 2,6-dichlorobenzoates and 99.0 parts of talc.

Wettable powders are in the form of finely divided particles which disperse readily in water or other dispersant. The wettable powder is ultimately applied to the plant either as a dry dust or as an emulsion in water or other liquid. Typical carriers for wettable powders include fuller's earth, kaolin clays, silicas, and other highly absorbent, readily wet inorganic diluents. Wettable powders normally are prepared to contain about 5% to 80% of active ingredient, depending upon the absorbency of the carrier and usually also contain a small amount of a wetting, dispersing or emulsifying agent to facilitate dispersion.

Other useful formulations for plant applications are the emulsifiable concentrates which are homogeneous liquid or past compositions which are dispersable in water or other dispersant and may consist entirely of an acetylenic 2,6-dichlorobenzoate with a liquid or solid or emulsifying agent or may also contain a liquid carrier such as xylene, heavy aromatic naphthas, isophorone and other non-volatile organic solvents. For plant application, these concentrations are dispersed in water or other liquid carrier and normally applied as a spray to the area to be treated. The percentage by weight of the essential active ingredient may vary according to the manner in which the composition is to be applied, but in general, comprises 0.005% to 95% of active ingredient.

Other useful formulations include simple solutions of the active ingredient in a dispersant in which it is completely soluble at the desired concentration, such as acetone or other organic solvents. Granular formulations wherein the chemical agent is carried on relatively coarse particles are of particular utility for aerial distribution or for penetration of cover crop canopy. Pressurized sprays, typically aerosols wherein the active ingredient is dispersed in finely-divided form as a result of vaporization of low boiling dispersant solvent carrier such as the freons, may also be used.

Of course, the formulations, concentration and mode of application of an acetylenic 2,6-dichlorobenzoate will be adapted to the particular plant and surrounding circumstances as is the case in all agronomic applications.

The active growth regulatory compound of this invention may be formulated and/or applied with other agricultural chemicals, such as insecticides, fungicides, nematocides, fertilizers and the like. In addition, combinations of an acetylenic 2,6-dichlorobenzoate with certain plant hormones, such as native auxins, anti-auxins, giberellins and kinins, may produce enhanced growth regulatory effects. It is apparent that modifications may be made in the formulation and application of the novel growth regulatory agent of this invention without departing from the invention concept herein.
What is claimed is:
1. A composition of matter having the formula
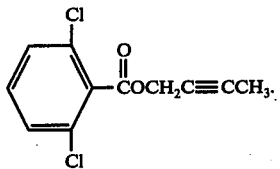
2. A composition of matter having the formula
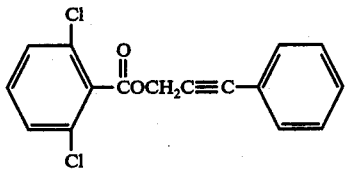
3. A composition of matter having the formula
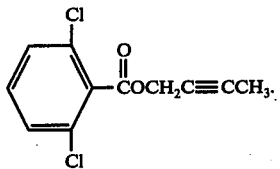
* * * * *